United States Patent [19]

Gavin et al.

[11] 4,078,000

[45] Mar. 7, 1978

[54] METHOD OF ISOLATING AND RECOVERING 2,4-DINITRO-N-SUBSTITUTED-1,3-PHENYLENEDIAMINE COMPOUNDS

[75] Inventors: David F. Gavin, Cheshire, Conn.; Delmer A. Fidler, Rochester, N.Y.; John H. Tobin, Beacon Falls, Conn.

[73] Assignee: Olin Corporation, New Haven, Conn.

[21] Appl. No.: 744,015

[22] Filed: Nov. 22, 1976

[51] Int. Cl.$^2$ .............................................. C07C 85/04
[52] U.S. Cl. .................................... 260/577; 260/573
[58] Field of Search .................. 260/573, 577; 71/121

[56] References Cited

U.S. PATENT DOCUMENTS

| | | |
|---|---|---|
| 3,257,190 | 6/1966 | Soper ............................. 260/577 X |
| 3,403,180 | 9/1968 | Soper ................................ 260/577 |
| 3,484,487 | 12/1969 | Dix ..................................... 260/577 |
| 3,617,250 | 11/1971 | Woods et al. ................... 260/577 X |
| 3,617,251 | 11/1971 | Hunter et al. .................. 260/577 X |
| 3,617,252 | 11/1971 | Hunter et al. .................. 260/577 X |
| 3,764,623 | 10/1973 | Hunter et al. ...................... 260/573 |
| 3,910,783 | 10/1975 | Hunter et al. .................. 260/577 X |
| 3,966,816 | 6/1976 | Woods et al. ...................... 260/573 |

*Primary Examiner*—Daniel E. Wyman
*Assistant Examiner*—Thomas A. Waltz
*Attorney, Agent, or Firm*—William A. Simons; Thomas P. O'Day

[57] ABSTRACT

Improved method of isolating and recovering 2,4-dinitro-N-substituted-1,3-phenylenediamine compounds having a trifluoromethyl substituent in the 6-position of the aromatic ring from the reaction medium.

10 Claims, No Drawings

METHOD OF ISOLATING AND RECOVERING 2,4-DINITRO-N-SUBSTITUTED-1,3-PHENYLENEDIAMINE COMPOUNDS

BACKGROUND OF THE INVENTION

I. FIELD OF INVENTION

This invention relates to an improved method of isolating and recovering 2,4-dinitro-N-substituted-1,3-phenylenediamine compounds having a trifluoromethyl substituent in the 6-position of the aromatic ring from the reaction medium.

II. DESCRIPTION OF THE PRIOR ART

U.S. Pat. Nos. 3,617,252 and 3,764,623 describe methods for making and using the above class of herbicidal compounds. These patents in their entirety are incorporated herein by reference. The above compounds are defined by the formula:

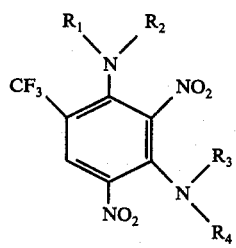

wherein $R_1$, $R_2$, $R_3$ and $R_4$ are each selected from hydrogen, lower alkyl, lower alkenyl, lower alkynyl, cyclo lower alkyl and cyclo lower alkenyl groups, said groups other than hydrogen being unsubstituted or having chloro, bromo, iodo, hydroxy or lower alkoxy substituents, with the proviso that at least one of $R_1$, $R_2$, $R_3$ or $R_4$ is not hydrogen. The lower alkyl, lower alkenyl, lower alkynyl and lower alkyoxy groups as used above are defined generally to have up to about six carbon atoms.

According to the cited prior art, the compounds of formula I are prepared generally by reacting a 3-halo-2,6-dinitro-4-trifluoromethylaniline compound with a stoichiometric excess of either ammonia, a primary amine or a secondary amine in the presence of an appropriate polar organic solvent (see equation A below).

While some members of this class of compounds have shown outstanding herbicidal properties, their widespread commercial acceptance has been somewhat hindered by troublesome processing conditions. This is especially true of the final isolation and recovery steps for making these herbicidal compounds. For instance, the above-cited patents only disclose recovering these compounds by first either water-washing or filtering techniques to remove by-product salts, followed by solvent evaporation and recrystallization steps. While these procedures may be suitable recovery methods for laboratory-scale experiments, they are often impractical on a layer commercial level. In particular, the commercial employment of a filtration step would require a great deal of solids handling and a follow-up step of vacuum drying the filtrate, both of which are costly, time-consuming and energy-intensive. Additionally, removal of the polar organic solvent by simple evaporation is time-consuming. Furthermore, it has been found, according to this invention, that the heat used in an evaporation step may have the effect of decomposing the product, thereby reducing the over-all yield.

Therefore, a need still exists in the art to improve the steps of isolating and recovering these compounds so that more attractive (i.e., less costly and higher yield) commercial products can be made. Such an improvement should also result in a lowering of the energy requirements and simplify the processing steps.

BRIEF SUMMARY OF THE INVENTION

The present invention is, therefore, directed to an improved process for isolating and recovering these herbicidal compounds from the solvent and other components of the reaction product mixture. Briefly, product isolation and recovery is achieved, according to this invention, by a process which comprises:

a. adjusting the pH of the reaction product mixture in the presence of water to between about 2.5 and about 7.5, b. azeotropically distilling said reaction product mixture in the presence of water to vaporize and remove substantially all of the polar organic solvent along with part of the water, leaving a residual mixture comprised of of water and the product, c. recovering the product from this mixture.

This isolation and recovery process, which is described in more detail below, meets the above-cited needs of the art and, moreover, has the advantage of being simple and economical, capable of being employed in one vessel, and not requiring either an expensive filtration or evaporation step.

DETAILED DESCRIPTION

The present invention encompasses isolating and recovering the above-defined herbicidal compounds shown in formula I and by U.S. Pat. Nos. 3,617,253 and 3,764,623. Typical examples of the groups represented by $R_1$, $R_2$, $R_3$ and $R_4$ in formula I are hydrogen and the lower alkyl, lower alkenyl, and lower alkynyl groups having up to about six carbon atoms, including the cyclic analogues thereof as well as the halo, hydroxy and lower alkoxy substituted derivatives thereof. Representative groups are methyl, ethyl, n-propyl, isopropyl, n-butyl, sec-butyl, n-pentyl, sec-pentyl, n-hexyl, allyl, 2-butenyl, 2-butynyl, 3-butynyl, methallyl, 2-pentynyl, 2-hydroxyethyl, 2-bromoethyl, 2-methoxyethyl, 3-ethoxypropyl, 2,2-dimethoxyethyl, 2-chloroallyl, 3-chloropropyl, 4hydroxy-2-butynyl, 1-methyl-2-methoxyethyl, 2-bromoallyl, propynyl, 4-chloro-2-butenyl, 4-bromo-1-butenyl, 3-iodo-2-pentenyl, 4-chloro-2-butynyl, cyclohexyl, cyclopropyl, cyclobutyl, cyclohexenyl and the like.

Further in formula I, $R_1$—$R_2$ and/or $R_3$—$R_4$ can represent a fragment of a ring of which the amino nitrogen is a part, such as illustrated by the structure:

in which Z is an alkylene group having from about two to six carbon atoms in the chain, and optionally other atoms such as oxygen and nitrogen. Such linkages include the dimethylene, trimethylene, tetramethylene, diethyleneoxy, diethyleneimino and hexamethylene groups. Thus, it is to be understood that, as used in the specification and claims herein, the definition of each of the four radicals $R_1$, $R_2$, $R_3$ and $R_4$ is intended to encompass cyclic or ring linkages.

A preferred class of compounds prepared by the process of this invention are those in which $R_1$ is hydrogen, $R_2$ and $R_3$ are each selected from hydrogen and alkyl of one to five carbon atoms and $R_4$ is alkyl of one to five carbon atoms. Thus, representative examples of alkyl are methyl, ethyl, n-propyl, isopropyl, sec-butyl, sec-pentyl and the like. More preferably, the total number of carbon atoms represented by $R_1 + R_2 + R_3 + R_4$ should be between two and eight. Compounds in which both $R_1$ and $R_2$ are hydrogen represent an especially preferred class.

In its most preferred embodiment, the invention is directed to the preparation and recovery of $N^3,N^3$-diethyl-2,4-dinitro-6-trifluoromethyl-1,3-phenylenediamine.

As shown in the above-cited patents, the reaction step of making these compounds comprises replacing a halogroup on the 1-position of the aromatic ring with the desired amino group (i.e., $-NR_1R_2$). This amino group is supplied from either ammonia, a primary amine or a secondary amine. The reaction is illustrated by equation A as follows:

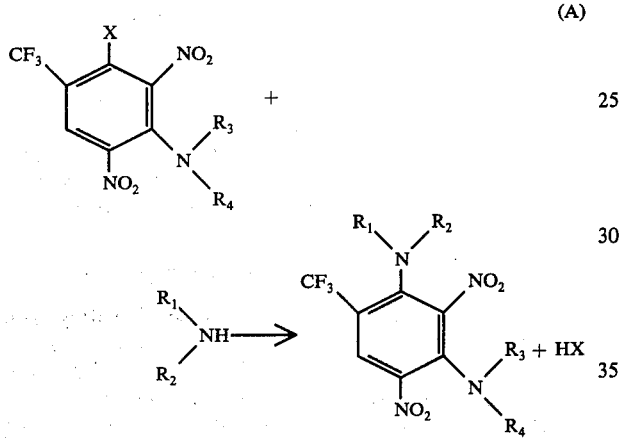

in which X is a reactive halogen such as chlorine or bromine and $R_1$, $R_2$, $R_3$ and $R_4$ have the significance previously assigned. Because the hydrogen halide formed by this reaction is hard to separate from the product and may cause some deposition and lower yields, it is very desirable to add the amine or ammonia in a great stoichiometric excess so that the hydrogen halide will react with it and form the corresponding amine halide or ammonium halide salt. This can be best represented by equation B as follows, wherein $R_1$, $R_2$ and X have the significance previously assigned.

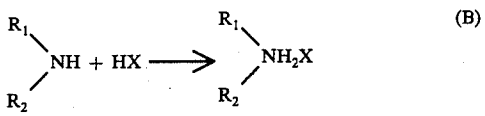

Additionally, other water-soluble by-products besides these by-product salts may also be present in the reaction product mixture. These include products of other side reactions, as well as impurities in the starting materials. Normally, these other components may be present in small amounts in the mixture.

The reaction shown in equation A is effected in the presence of one or more appropriate organic solvents. Any polar organic solvent may be employed (1) which is inert to, or unreactive with the reaction system, (2) which is capable of at least partially, preferably completely, dissolving the amine or ammonia reactant, and (3) which forms an azeotrope with water having a boiling point suitably below the boiling point of water so that the azeotropic distillation step discussed below can be carried out. Thus it is to be understood that, as described in the specification and claims herein, the term "polar organic solvent" is intended to refer to those solvents having the above characteristics. The solvents include the protic and aprotic liquids such as the oxygenated organic solvents illustrative of which are the simple alcohols, the ketones, ethers and the like.

Preferred are the aliphatic and cycloaliphatic, oxygenated polar solvents, especially, for example, lower alcohols and ethers.

Specific illustrations of applicable solvents include:

tetrahydrofuran
dioxane
diisopropylether
diethylether
glycol ethers
methanol
ethanol
isopropanol
n-propanol
t-butanol
sec-butanol
n-butanol
acetone
methylethyl ketone
methylisopropyl ketone The most preferred polar organic solvents are tetrahydrofuran and methanol.

Preferably, water is also employed in the reaction medium in combination with the organic solvent to aid in dissolution of water-soluble matter present in the reaction system. The water also provides a better medium for bringing the amine or ammonia reactant into intimate contact with the organic substrate so that the reaction will occur at a more economically feasible rate. However, the use of water in the reaction, although preferred, is not necessary. Moreover, the optimum amounts of any of the various solvents discussed relative to the reactants are to be determined for each particular reaction and are not critical limitations of the present invention.

Other details and parameters, e.g., reaction temperature for effecting the reaction represented by equation A above are described in the above-cited patents which are incorporated by reference herein.

At the end of the reaction shown by equation A, a reaction product mixture is obtained which comprises several constituents. These embrace, along with the desired product, the organic solvent, unreacted amine or ammonia ($NHR_1R_2$), and water-soluble by-products such as the by-product salts as illustrated in equation B. If water was used in effecting the reaction, this would of course also be present. The object of the invention is to isolate and recover the desired product from these other constitutions of the reaction product mixture.

The first critical step of the present invention is to adjust the pH of the reaction product mixture in the presence of water to between about 2.5 and about 7.5, preferably about 5.0–7.0, and most preferably 5.5–6.5. This adjustment of pH has the functions of (1) effecting transfer of the water-soluble by-products and, especially, the excess $NHR_1R_2$ from the organic reaction product mixture into the water or aqueous phase, and (2) rendering innocuous some of the impurities (e.g., nitrogen based compounds such as $NH_3$) in the reaction product mixture which would otherwise attack the desired product, thereby degrading it. The presence of water is necessary here so that the water-soluble by-products and excess $NHR_1R_2$ compounds can be transferred to and dissolved therein. So if water was not employed or employed only in small amounts during the reaction, sufficient amounts should be added prior to the acid adjustment so that the water-soluble matter and excess $NHR_1R_2$ compounds can be dissolved therein. If sufficient water was employed in the reaction or in the preferred preliminary steps discussed below and is still present with the reaction product mixture, there is no need to add anymore.

The adjustment of pH can be achieved by any suitable or conventional technique. The usual technique is to add small amounts of dilute acid, e.g., dilute aqueous hydrochloric acid, to the basic reaction product mixture until the requisite pH is achieved. Caution should be exercised in such practice to avoid addition of too much acid (i.e., lowering the pH to below about 2.5) because then the acid may attack the product or solubilize the desired product as a salt, resulting in a lower yield.

Before carrying out the first step of pH adjustment, it is desirable to employ one or more preliminary steps to expedite or facilitate the subsequent removal of excess reactant and water-soluble matter present. One such step is venting off the gases that are present, e.g., ammonia or amine. Another step is to subject the reaction product mixture to a water-washing operation in order to remove a substantial portion of the water-soluble components.

After the pH adjustment, the next necessary step of the present invention is to azeotropically distill the reaction product mixture in the presence of water to vaporize and remove substantially all of the polar organic solvent along with part of the water, leaving a residual mixture comprised of water and the product. Essentially the function of this step is a solvent exchange. The organic solvent which has always been present with the product is now removed and replaced with water. Azeotropic distillation is defined herein in its conventional sense, that is, at a particular temperature, an azeotrope of water and polar organic solvent will be formed which will distill off. Usually, the distillation temperature, while dependent on the solvent, will start at about 70° C at atmospheric pressure and go up. When the distillation temperature approaches about 99°–100° C, substantially all of the polar organic solvent will have been boiled off with part of the water. One advantage of this step is, that unlike solvent evaporation, it avoids dry-heating a "dinitrobenzene" compound which can easily cause decomposition of the product, thereby lowering yields and purity.

If desired, the azeotropic distillation step may be preceded by phase separation wherein the aqueous phase containing dissolved water-soluble matter is removed. When this is done, it will of course be necessary to add fresh amounts of water to the organic phase before commencing the azeotropic distillation. Alternatively, the water can be introduced as a gaseous stream.

In effecting the azeotropic distillation step, it is generally preferable to add more water as the distillation progresses to substantially complete removal of the solvent. It is also advisable to continuously monitor the pH of the mixture during the azeotropic distillation and, if necessary, adjust it to within the range specified above. The solvent/water distillate need not be discarded, but rather it may be captured for re-use as a medium in subsequent repeat reactions.

The final step of the present invention is simply recovering the product from this mixture. Because the product is insoluble in water, it will form a separate, lower layer as soon as the distillation is stopped. If the temperature of the vessel is kept above the crystallization temperature of the product, it will remain in a liquid state. Then the phase separation is preferably brought about by simply draining the product from the bottom of the vessel. If the temperature is below the crystallization temperature, the product will be solid and the water is preferably decanted or pumped off. Removal of the water in this step would also entail removing any slight amounts of $NHR_1R_2$ and by-product salt impurities which may be still present therein.

After the above isolation process, the product is then preferably formulated with conventional herbicide formulae or stored in its pure solid or liquid state. The cited prior art shows many examples of such formulations.

Thus, as can be seen, the present invention is carried out without the disadvantages of employing either filtration or evaporation steps. Moreover, the resulting product is essentially free of both water and organic solvents. Also, the present process is both cost-saving and time-saving in that the whole recovery method can be carried out quickly in one reactor or vessel. This further results in a reduced capital expenditure. And, while the present isolation and recovery process is preferably carried out in a liquid state during all three steps, the invention also includes recovering those compounds that may be either semi-solids (e.g., thick oils) or solids. In those cases, the product may be present as a solid throughout the process, rather than be dissolved in the organic layer.

A preferred example of a compound that can be recovered by the present process is $N^3,N^3$-diethyl-2,4-dinitro-6-trifluoromethyl-1,3-phenylenediamine. By keeping the temperature of the above steps in a range from about 60°–100° C, and, most preferably, around 90°–95° C for the third step, this compound can be recovered as a liquid.

The following examples further illustrate the present invention, isolating and recovering this compound. All percentages and proportions are by weight unless expressly stated otherwise.

EXAMPLE 1

$N^3,N^3$-diethyl-2,4-dinitro-6-trifluoromethyl-1,3-phenylenediamine was made in a one liter Parr stirred autoclave reactor by first charging therein 152.0 grams of N,N-diethyl-3-chloro-2,6-dinitro-4-trifluoromethylaniline, 312 grams tetrahydrofuran and 22.5 grams of water. Then, the reaction was sealed and cooled to about 15° C. Anhydrous ammonia was pressurized until a constant 60–65 psig was obtained at the same temperature. The reaction was allowed to run to 6.0 hours.

Then the reactor was vented and excess ammonia and tetrahydrofuran gases were allowed to escape while the reactor temperature reached 25° C. The liquid reaction product was diluted with about 120 ml of water and two finite layers were obtained. These were phase separated from each other. The water portion (226.2 gms) was discarded. The organic layer (355 gms) was added to fresh water (300 gms). This mixture was pH adjusted to 6.5 with 37% HCl. Again the two layers were phase separated and the water layer was discarded. The organic layer was again added to fresh water and this mixture was subjected to azeotropic distillation. The tetrahydrofuran was removed as a water azeotrope until the temperature of the overhead vapors was 100° C. Fresh make-up water was added to the distillation apparatus as the azeotrope was removed.

The residual mixture was cooled to 95° C and two liquid phases were allowed to separate. The lower organic phase (132 gms) was separated from the water. The yield of the bottom layer was 90% by weight based on the amount of reactants used. Analysis of this bottom layer showed that 88.1% by weight was the desired $N^3,N^3$-diethyl-2,4-dinitro-6-trifluoromethyl-1,3-phenylenediamine. The amounts of tetrahydrofuran, by-product salt, $NH_3$ and water were all negligible.

EXAMPLE 2

$N^3,N^3$-diethyl-2,4-dinitro-6-trifluoromethyl-1,3-phenylenediamine was prepared in a Parr reactor using the same amounts of reactants and solvents as in Example 1, except the reaction was carried out at 50° C using anhydrous ammonia gas in amounts sufficient to create 80 psig pressure. After the reaction had been completed, the reactor was cooled to 25° C and vented. Without adding any additional water, the water layer was separated from the organic by phasing. Then, 150 ml of fresh water was added and the pH of the resulting mixture was adjusted to 6.1 using 37% aqueous HCl. The water layer was then phased from the bottom organic layer. Then, 450 ml of water was charged to the organic layer and the mixture was subjected to azeotropic distillation until the overhead vapor temperature was 100° C. Fresh water was added during distillation. The distillate was discarded and the residue was collected and allowed to settle and cool at 95° C, and two liquid phases were allowed to separate. The lower organic layer yielded 121.4 gms which was a yield of roughly 80 to 85% by weight based on the weight of the reactants. This organic phase was allowed to solidify at 25° C and analysis thereof showed negligible amounts of tetrahydrofuran, by-product salts, $NH_3$ and water.

EXAMPLE 3

The same compound was produced by the same reaction conditions as shown in Example 2. After the reaction was completed, the reactor was cooled to 25° C and the ammonia and other gases were vented. The crude reaction mixture was diluted with 135.5 grams of water. The resulting water layer was then phase separated from the organic layer. Then 150 gm. of fresh water was added to the organic layer. The pH of this mixture was adjusted to 6.0 with 37% aqueous HCl. Again, the water layer was removed by a phase separator. Fresh water (450 gm.) was added to the organic layer and the mixture gradually heated to 100° C while removing a water/tetrahydrofuran azeotrope. When the temperature of the overhead vapors reached 100° C, the distillation was stopped and the reactor was cooled to 95° C. The organic layer was then allowed to settle to the bottom and was then drained off. The desired product was isolated in a 90% by weight yield based on the amount of reactants employed. The amounts of tetrahydrofuran, $H_2O$, by-product salts and $NH_3$ present in the organic layer were negligible.

What is claimed is:

1. In a process for preparing a compound of the formula:

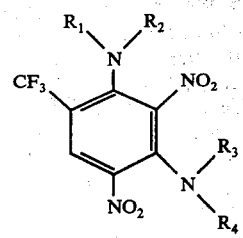

which comprises reacting
(1) a compound of the formula:

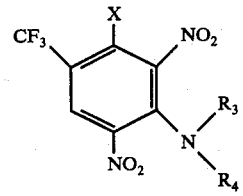

with
(2) a stoichiometric excess of an amine or ammonia as represented by the formula:

wherein, as applied to said formulas, $R_1$, $R_2$, $R_3$ and $R_4$ are each selected from hydrogen, lower alkyl, lower alkenyl, lower alkynyl, cyclo lower alkyl and cyclo lower alkenyl groups, said groups other than hydrogen being unsubstituted or having chloro, bromo, iodo, hydroxy or lower alkoxy substituents, with the proviso that at least one of $R_1$, $R_2$, $R_3$ or $R_4$ is not hydrogen; and X is a reactive halogen; said reaction being carried out in the presence of a polar organic solvent and resulting in a reaction product mixture comprised of a compound of said formula I, unreacted $NHR_1R_2$, said organic solvent and water-soluble by-products, the improvement for isolating and recovering said compound of formula I which comprises:
 a. adjusting the pH of the reaction product mixture in the presence of water to between about 2.5 and about 7.5,
 b. azeotropically distilling said reaction product mixture in the presence of water to vaporize and remove substantially all of said polar organic solvent along with part of the water, leaving a residual mixture comprised of water and said compound of formula I, and
 c. recovering said compound of formula I from said residual mixture.

2. The process of claim 1 wherein said compound is $N^3,N^3$-diethyl-2,4-dinitro-6-trifluoromethyl-1,3-phenylenediamine.

3. The process of claim 2 wherein said organic solvent is selected from a group consisting of tetrahydrofuran and methanol.

4. The process of claim 1 which comprises the added step of after said pH adjustment, separating an aqueous phase containing said water-soluble by-products from an organic phase containing said polar organic solvent and said compound of formula I.

5. The process of claim 4 wherein the pH of said liquid mixture is adjusted to from about 5.0 to about 7.0.

6. The process of claim 5 wherein said compound of formula I is recovered in step (c) by liquid phase separation from said water.

7. The process of claim 1 wherein said process is carried out at a temperature so that said compound of formula I is liquid throughout said isolation and recovery process.

8. The process of claim 1 wherein said compound of formula I is selected from a group of compounds wherein $R_1$ is hydrogen, $R_2$ and $R_3$ are each selected from hydrogen and alkyl of one to five carbon atoms and $R_4$ is an alkyl of one to five carbon atoms.

9. In a process for preparing $N^3$, $N^3$-diethyl-2,4-dinitro-6-trifluoromethyl-1,3-phenylenediamine which comprises reacting N,N-diethyl-3-chloro-2,6-dinitro-4-trifluoromethylaniline with a stoichiometric excess of $NH_3$ in the presence of a solvent selected from a group consisting of tetrahydrofuran and methanol to form a reaction product mixture comprising said $N^3,N^3$-diethyl-2,4-dinitro-6-trifluoromethyl-1,3-phenylenediamine, said solvent $NH_3$ and water-soluble by-products, wherein the improvement comprises:

isolating and recovering said $N^3,N^3$-diethyl-2,4-dinitro-6-trifluoro-1,3-phenylenediamine from the other constituents of said reaction product mixture by the process comprising:

a. venting $NH_3$ and solvent gases from said reaction product mixture, b. adding water to said reaction product mixture to form a liquid mixture containing an aqueous phase and an organic phase, then separating said aqueous phase from said organic phase, thereby removing water-soluble by-products and $NH_3$ from the organic phase, c. adding water to said organic phase to form a second liquid mixture containing an aqueous phase and an organic phase, adjusting the pH of said second liquid mixture to from about 5.0 to about 7.0, then separating said aqueous phase from said organic phase, d. adding water to said organic phase to form a third liquid mixture and azeotropically distilling said third liquid mixture to vaporize and thereby remove part of said water along with substantially all of said solvent, leaving a residual mixture containing water and $N^3,N^3$-diethyl-2,4-dinitro-6-trifluoromethyl-1,3-phenylenediamine, and e. recovering said $N^3,N^3$-diethyl-2,4-dinitro-6-trifluoromethyl-1,3-phenylenediamine from said third mixture.

10. The process of claim 8 wherein the pH is adjusted to from about 5.5 to about 6.5.

* * * * *